US00PP33793P2

(12) United States Plant Patent
Schoone

(10) Patent No.: US PP33,793 P2
(45) Date of Patent: Dec. 28, 2021

(54) ***PHALAENOPSIS* PLANT NAMED 'STRANGE MAGIC'**

(50) Latin Name: *Phalaenopsis hybrida*
Varietal Denomination: Strange Magic

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,963

(22) Filed: Jun. 5, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on phalaenopsis plant named, 'Strange Magic', QZ PBR 2020/2195, filed Sep. 17, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Strange Magic', characterized by its upright plant habit; moderately vigorous to vigorous growth habit; strong flowering stems; strong leaves; freely flowering habit with typically two inflorescences per plant, each inflorescence with numerous flowers; large light reddish purple-colored flowers with greenish white-colored spots with dark red-colored central dots; and good postproduction longevity.

2 Drawing Sheets

Figure 1:
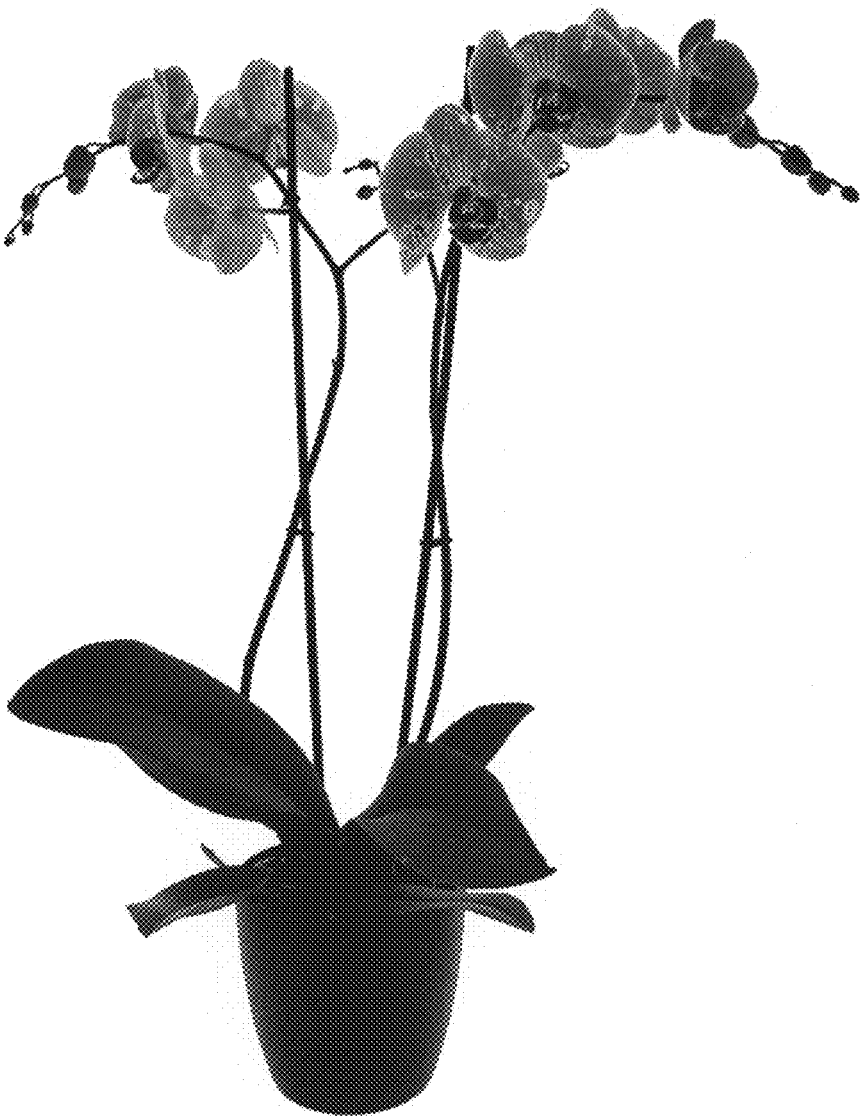

Botanical designation: *Phalaenopsis hybrida.*
Cultivar denomination: 'STRANGE MAGIC'.

CROSS-REFERENCED TO CLOSELY-RELATED APPLICATIONS

Title: Varieties of *Phalaenopsis* Plants
Inventor: René Schoone
Filed: Jun. 6, 2020
Ser. No.: 62/705,003
Inventor and Applicant/Assignee hereby claims the benefit of this provisional U.S. Patent Application.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2195. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Strange Magic'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in April, 2014 in De Lier, The Netherlands of a proprietary selection of *Phalaenopsis hybrida* identified as code number G 4018, not patented, as the female, or seed, parent with a proprietary selection of *Phalaenopsis hybrida* identified as code number Lee 1159, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Strange Magic'. These characteristics in combination distinguish 'Strange Magic' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large light reddish purple-colored flowers with greenish white-colored spots with dark red-colored central dots.
7. Good postproduction longevity.

Plants of the new *Phalaenopsis* can be compared to plants of the female parent selection. Plants of the new *Phalaenopsis* differ primarily from plants of the female parent selection in flower color as flowers of plants of the new *Phalaenopsis* have fewer spots than flowers of plants of the female parent selection. In addition, the curvature of the labellum is stronger in plants of the new *Phalaenopsis* than plants of the female parent selection.

Plants of the new *Phalaenopsis* can be compared to plants of the male parent selection. Plants of the new *Phalaenopsis* differ primarily from plants of the male parent selection in flower color as flowers of plants of the new *Phalaenopsis* have fewer spots than flowers of plants of the male parent selection. In addition, the petal spots of plants of the new *Phalaenopsis* are greenish white in color with dark red-colored central dots whereas petal spots of plants of the male parent selection are red in color.

Plants of the new *Phalaenopsis* can be compared to plants of *Phalaenopsis hybrida* 'Iconia', not patented. In side-by-side comparisons, plants of the new *Phalaenopsis* differ primarily from plants of 'Iconia' in flower color as flowers of plants of the new *Phalaenopsis* have fewer spots than flowers of plants of 'Iconia'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Strange Magic' grown in a container.

Figure 2:
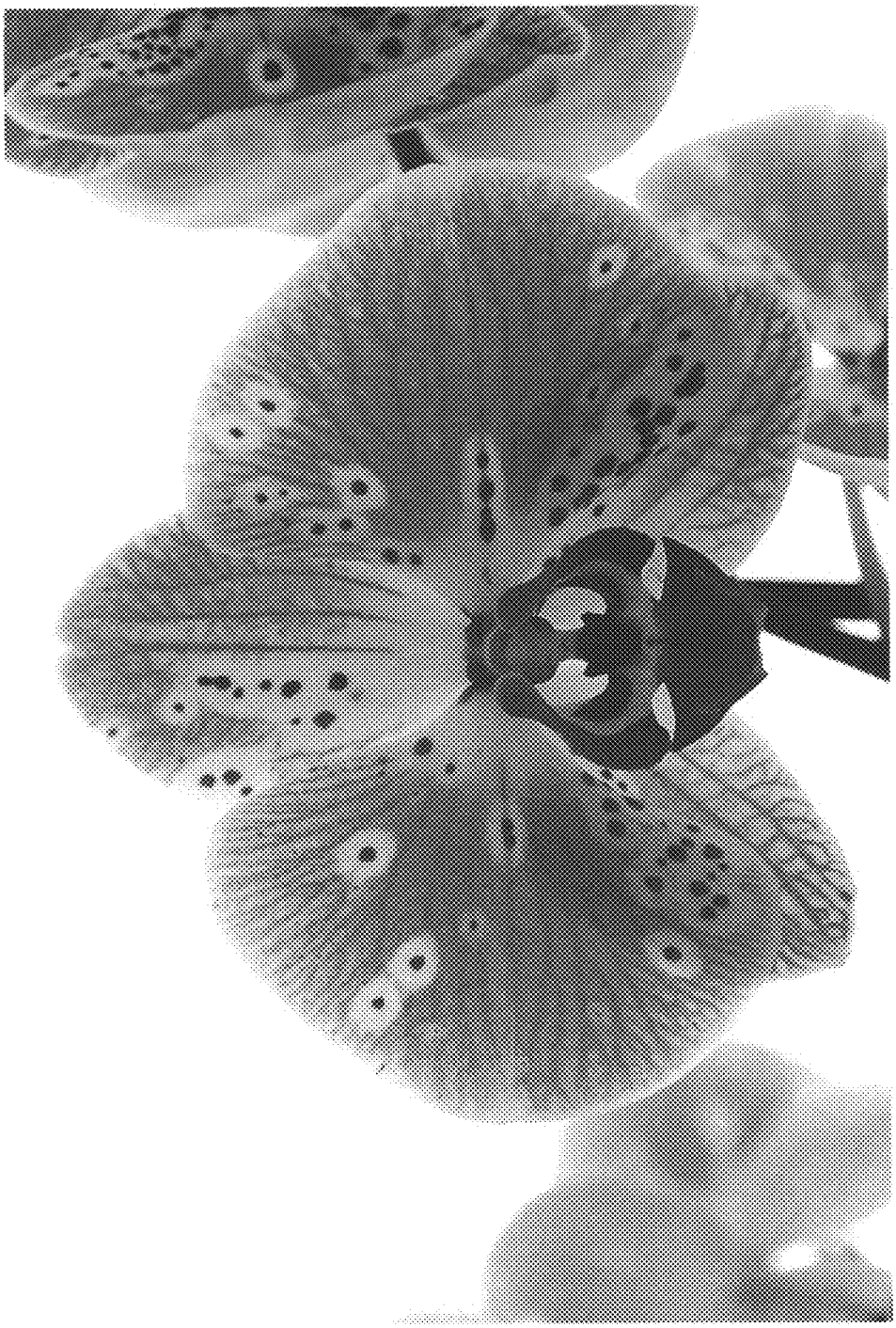

The photograph on the second sheet (FIG. 2) is a close-up view of a typical flower of 'Strange Magic'.

DETAILED BOTANICAL DESCRIPTION

The aforementioned photographs and following observations and measurements describe plants grown during the late autumn and early winter in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Strange Magic'.

Parentage:

*Female parent*.—Proprietary selection of *Phalaenopsis hybrida* identified as code number G 4018, not patented.

*Male parent*.—Proprietary selection of *Phalaenopsis hybrida* identified as code number Lee 1159, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 16 cm.

*Plant height, substrate level to top of inflorescences*.—About 52.5 cm.

*Plant diameter or spread*.—About 41.6 cm.

Leaf description:

*Arrangement and quantity*.—Distichous, simple; sessile; about six leaves per plant.

*Length*.—About 22.7 cm.

*Width*.—About 7.5 cm.

*Aspect*.—Upright to outwardly arching.

*Shape*.—Ovate to lanceolate to narrowly oblong; slightly carinate.

*Apex*.—Unequal acute to unequal broadly acute.

*Base*.—Sheathing. Sheath length: About 1.8 cm. Sheath width: About 1.3 cm. Sheath color: Close to 143C; towards the distal margin, close to 143A to 143B.

*Margin*.—Entire; slightly undulate.

*Texture and luster, upper and lower surfaces*.—Smooth, glabrous; slightly glossy.

*Venation pattern*.—Camptodromous.

*Color*.—Developing leaves, upper surface: Close to NN137B. Developing leaves, lower surface: Close to 146A. Fully expanded leaves, upper surface: Close to NN137B slightly tinged with close to 146A; venation, close to NN137A. Fully expanded leaves, lower surface: Close to between 144A and 146B; towards the margins, close to 137B; venation, close to 143A.

Inflorescence description:

*Appearance and flowering habit*.—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 28.2 cm.

*Inflorescence width*.—About 20.1 cm.

*Flower buds*.—Height: About 2 cm. Diameter: About 1.5 cm by 1.6 cm. Shape: Broadly ovate. Color: Close to 146D tinged with close to 174A.

*Flower size*.—Large, about 7.8 cm (vertical) by 9.8 cm (horizontal).

*Flower depth*.—About 3.6 cm.

*Petals, quantity and arrangement*.—Three, two lateral petals and one center petal transformed into a labellum.

*Lateral petals*.—Length: About 4.6 cm. Width: About 5.8 cm. Shape: Reniform to broadly rhomboidal. Apex: Shallowly retuse. Margin: Entire. Texture and luster, upper and lower surfaces: Smooth, glabrous, velvety; matte. Color: When opening, upper surface: Close to N78B; towards the margins, close to N78C to N78D; towards the base, close to 157B to 157C and at the base (at column connection), close to N79B to N79C; moderately spotted, spots, variable and random, close to 157D each spot with a smaller central dot, close to between 59A and 187B to 187C; venation, close to N78A to N78B. When opening, lower surface: Close to 75A and N75A; towards the margins, close to 157A; towards the base, close to 149D; moderately spotted, spots, variable and random, close to 157A, each spot with a smaller central dot, close to 183D to lighter than 183D; venation, close to N78B. Fully opened, upper surface: Ground color, close to 76B to 75D overlain with close to between N78B and NN78C; towards the margins and base, close to N155A and NN155B; at the base (at column connection), close to N79C; moderately spotted, spots, variable and random, close to NN155D each spot with a smaller central dot, close to 187C; venation, close to N78A to N78B. Fully opened, lower surface: Close to N78C and N75B; towards the margins and base, close to 155C; moderately spotted, spots, variable and random, close to NN155B, each spot with a smaller central dot, close to 183D to lighter than 183D; venation, close to N78A to N78B.

*Labella*.—Appearance: Three-parted with two lateral lobes and a central lobe. Length, lateral lobes: About 2.4 cm. Width, lateral lobes: About 1.6 cm. Length, central lobe: About 3.7 cm. Width, central lobe: About 6 mm to 22 mm. Shape, lateral lobes: Obovate. Shape, central lobe: Deltoid. Apex, lateral lobes: Obtuse. Apex, central lobe: Cleft with two narrow and strongly recurved cirrose tips, about 1.7 cm in length and about 1.7 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 6 mm in width and about 5 mm in height. Color: When opening, upper surface: Lateral lobes: Close to 70A and lower third, close to 155A; basal margin, close to 59A to 59B and tinged with close to 12A; blotches, close to 59A. Central lobe: Close to 59B; distally, close to 59C; at the base, close to 187A and 157D; main vein, close to 183B; cirrose tips, close to 59A. Callosities: Close to 10C; distally, close to 187A. When opening, lower surface: Lateral lobes: Close to 70A and lower third, close to 156D; basal margin, close to 59A to 59B tinged with close to 12A. Central lobe: Close to 59B; distally, close to 61A and 70A; at the base, close to 156D and 157B; main vein, close to N79C; cirrose tips, close to 61A. Fully opened, upper surface: Lateral lobes: Close to 70A and lower third, close to 155A; basal margin, close to 59A to 59B and tinged with close to 12A; blotches, close to 59A. Central lobe: Close to 59B; distally, close to 60C; at the base, close to N186C and 157D; main vein, close to 183A; cirrose tips, close to 59A. Callosities: Close to 8B; distally, close to N186C. Fully opened, lower surface: Lateral lobes: Close to 70A and lower third, close to 156D; basal margin, close to 59A to 59B tinged with close to 12A. Central lobe: Close to 59B; central band, close to N78A and N78B with a distal blotch, close to NN155D; at the base, close to 156D and 157B; cirrose tips, close to 71A.

*Sepals*.—Quantity and arrangement: Three, one upper dorsal sepal and two lower lateral sepals. Length, dorsal sepal: About 4.6 cm. Width, dorsal sepal: About 3.2 cm. Length, lateral sepals: About 4.8 cm. Width, lateral sepals: About 3 cm. Shape, dorsal sepal: Broadly elliptic to slightly obovate. Shape, lateral sepals: Ovate. Apex, dorsal sepal: Shallowly emarginate. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N78C;

towards the margins, close to N78D and edges, close to 157A to 157B; towards the base, close to 157A to 157B and at the base (at column connection), close to 70A; slightly and variably dotted, dots, close to between 59A and 187B to 187C; venation, close to 70A and 71A. When opening, lower surface: Close to between 153C and 195B; towards the margins, close to 182D and edges, close to 149D to lighter than 149D; basal blotch, close to N79B. Fully opened, upper surface: Close to N78B to N78C; towards the margins and base, close to NN155C; at the base (at column connection), close to N79C; slightly and variably blotched, blotches, close to NN155C each blotch with a smaller central dot, close to between N79C and 187B to 187C; venation, close to N78A and NN78A. Fully opened, lower surface: Close to N80D; tinged towards the base with close to 150D and edges, close to 155C; central blotch, close to 152D; few small basal dots, close to N79B. Color, lateral sepals: When opening, upper surface: Close to between 72B and N78B; lower third, close to 150C and between 150D and 157B; towards the margins, close to 149D; at the base (at column connection), close to 70B; slightly spotted, spots, variable and random, close to between 59A and 187B to 187C; venation, close to N78A. When opening, lower surface: Close to between 152D and 195A; at the edges, close to 149D; venation, close to 182B. Fully opened, upper surface: Close to 157B to 157C; towards the base, close to 150C to 150D and at the base (at column connection), close to N79B to N79C; slightly spotted, spots, variable and random, close to between 59A and 187B to 187C; venation, close to between N78A and NN78A. Fully opened, lower surface: Close to between 148D and 195B; at the edges, close to between 149D and 150D; venation, close to N78D.

*Peduncles*.—Length: About 63 cm. Diameter: About 5 mm. Strength: Strong. Aspect: Upright to outwardly arching. Texture and luster: Smooth, glabrous; matte. Color: Close to between 200A and 202A with fine dots, close to 147B to 147C.

*Pedicels*.—Length: About 3.6 cm. Diameter: About 3 mm. Strength: Moderately strong. Aspect: About 80° from peduncle axis. Texture and luster: Smooth, glabrous; matte. Color: Close to 147D; proximally, close to 146C.

*Reproductive organs*.—Androecium: Column length: About 1 cm. Column width: About 6 mm. Column color: Close to N78A and distally, close to 76A to 76D. Pollinia quantity: Two. Pollinia diameter (per two pollinia): About 3 mm. Pollinia color: Close to N25B. Gynoecium: Stigma length: About 4 mm. Stigma width: About 5 mm. Stigma shape: Reniform. Stigma color: Close to N155A; edges, close to 77A. Ovary length: About 6 mm. Ovary diameter: About 1 mm. Ovary color: Close to 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Strange Magic' as illustrated and described.

* * * * *